United States Patent
Rettberg et al.

(10) Patent No.: US 11,465,149 B2
(45) Date of Patent: Oct. 11, 2022

(54) CONTAINER CAP LINER FOR VIALS CONTAINING VOLATILE AND GAS COMPOUNDS

(71) Applicant: LGC North America Inc., Manchester, NH (US)

(72) Inventors: Thomas M. Rettberg, Weare, NH (US); Kengkaj Sukcharoenphon, Amherst, NH (US); Daniel Biggerstaff, Mt. Pleasant, SC (US)

(73) Assignee: LGC NORTH AMERICA INC., Manchester, NH (US)

( * ) Notice: Subject to any disclaimer, the term of this patent is extended or adjusted under 35 U.S.C. 154(b) by 963 days.

(21) Appl. No.: 15/995,011

(22) Filed: May 31, 2018

(65) Prior Publication Data

US 2019/0366327 A1 Dec. 5, 2019

(51) Int. Cl.
*B01L 3/00* (2006.01)
*G01N 33/18* (2006.01)

(52) U.S. Cl.
CPC .......... *B01L 3/508* (2013.01); *G01N 33/1826* (2013.01); *B01L 2300/042* (2013.01)

(58) Field of Classification Search
CPC ............ B01L 3/50825; B01L 2300/04; B01L 2300/042; B01L 2300/044; B01L 3/508; B01L 5/02; B01D 41/023; B01D 41/0421; B01D 41/0457; B65D 41/023; B65D 41/0421; B65D 41/0457
See application file for complete search history.

(56) References Cited

U.S. PATENT DOCUMENTS

| 3,976,217 | A | 8/1976 | Dukess | |
|---|---|---|---|---|
| 5,297,433 | A | 3/1994 | Elgas | |
| 5,456,126 | A | 10/1995 | Suddath | |
| 2003/0222046 | A1* | 12/2003 | Schenck | B65D 41/0407 215/341 |
| 2008/0078737 | A1* | 4/2008 | Brennan | B65D 39/0058 215/364 |
| 2009/0196798 | A1* | 8/2009 | Sassa | A61J 1/1406 422/400 |
| 2009/0208729 | A1* | 8/2009 | Allegaert | B32B 5/18 428/319.9 |

FOREIGN PATENT DOCUMENTS

| CN | 2654528 Y | 11/2004 |
|---|---|---|
| CN | 202368918 U | 8/2012 |
| EP | 357663 A1 | 8/1998 |

OTHER PUBLICATIONS

NovaSeptum® Bottle Sampling Unit, Specification Sheet, EMD Millipore, 2 pp.

(Continued)

*Primary Examiner* — Jill A Warden
*Assistant Examiner* — Dwayne K Handy
(74) *Attorney, Agent, or Firm* — Grossman, Tucker, Perreault & Pfleger, PLLC

(57) ABSTRACT

A container cap liner that that facilitates the storage of gases and various volatile organic compounds (VOCs). More particularly, the container cap liner reduces the loss of gases and various volatile compounds thereby providing for relatively longer storage periods with relatively more accurate analytical analysis.

14 Claims, 3 Drawing Sheets

(56) References Cited

OTHER PUBLICATIONS

Kynar PVDF gas sampling bag with PTFE valve & septum port syringe sampling+PTFE fitting KYN3Z_0.5L (air sample bag), Hedetech, 3 pp.
Tedlar® Film Use in Gas Sampling Bags, American Durafilm Blog, Aug. 11, 2016, 4 pp.
European Search Report dated Mar. 9, 2020 relating to corresponding European Application No. 19 177 443.9.

* cited by examiner

— Liner

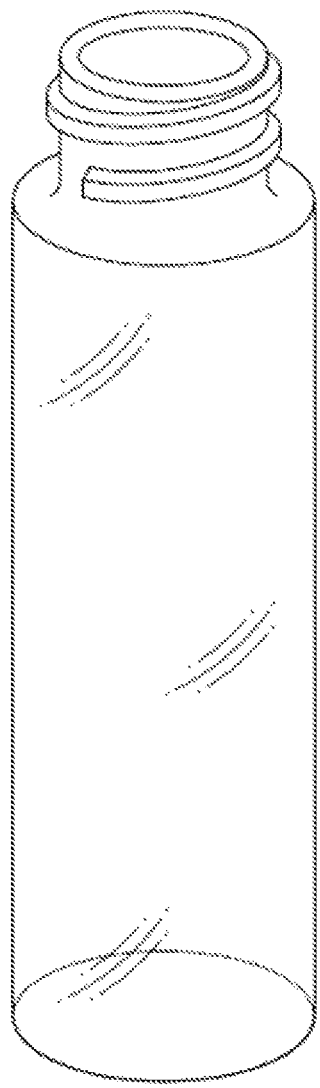
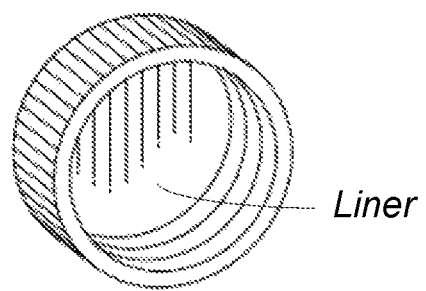
FIG. 4
FIG. 5

CONTAINER CAP LINER FOR VIALS CONTAINING VOLATILE AND GAS COMPOUNDS

FIELD

The present invention is directed at a container cap liner that that facilitates the storage of gases and various volatile organic compounds (VOCs). More particularly, the container cap liner reduces the loss of gases and various volatile compounds thereby providing for relatively longer storage periods with relatively more accurate analytical analysis.

BACKGROUND

The measurement of volatile organic compounds (VOCs) in groundwater is an important test that is conducted by numerous laboratories throughout the world. In more recent prominence is the need to test samples for pre-drill and post-drill aquifer monitoring in localities where hydraulic fracturing for shale gases is occurring. Groundwater wells in regions having coalbed methane production are also commonly tested. An estimated testing 2000 wells in the US were tapped in 2016 and an estimated 300,000 samples of groundwater are tested annually for VOC content.

Currently, multiple analytical methods for dissolved gases in liquid matrices are available utilizing gas chromatography (GC), including ASTM D8028, PA DEP 3686, USEPA RSK 175. These are headspace GC techniques and commonly and reliably employed for tests such as blood alcohol and pharmaceutical impurity volatiles testing. However, for VOC applications these methods are replete with well documented variability between laboratories for measured values. In 2017 at the National Environmental Monitoring Conference (Washington, D.C.) it was reported that the variability of measurement results for methane between fourteen laboratories was over a factor of five (7440 parts per million to 34,600 parts per million for fresh control samples split between these laboratories). Amongst the root causes of the poor agreement between laboratories is the lack of a suitable, stable reference material from which to calibrate or verify calibration of the analytical instrumentation. In analytical chemistry and particularly with electronic instrumentation, the use of Certified Reference Materials (CRM) and Performance Testing (PT) samples is the foundation of consistent analytical data and is a core function of bodies such as the US National Institute of Science and Technology's (NIST) Standard Reference Material (SRM) program and commercial laboratories to provide such materials. These reference chemicals are supplied with certified concentrations within a stated shelf life and are used to create or verify instrument calibration. The absence of CRM for this acutely important test is a serious impediment to accurately assessing groundwaters in the US for volatile organics; especially significant for test samples from "fracking" regions.

Methane and other relatively low molecular weight, non-polar hydrocarbons are considered either non-soluble or poorly soluble in water and creating mixtures of these gases in water require the correct chemical and physical conditions of pressure, concentration (exposure), temperature, and confinement in a system or container. Hence, groundwater or artificially produced solutions of methane and other VOC's have inherent instability with the outcome being outgassing of the volatile component from the matrix. Therefore, the collection and retention of the field samples, calibrants or reference materials is a key problem and has forced particularly strict guidelines for storage and handling of these mixtures. The analytical methods cited earlier specify storage times for solutions between 7 and 14 days under cold (6° C.) conditions. Calibration standards or calibration verification standards are typically prepared fresh by arduous methods that require pre-blended or pure forms of the hydrocarbon analytes (i.e. gas cylinders) to be available in each laboratory and typically rely on imperfect application of ideal gas laws (e.g. Henry's Law, Raoult's Law) and bubbler or static exposures to produce an assumed saturated solution from which dilutions are made. Alternative suppliers of standards such as the NIST SRM program, other NMI (national measurement institute) materials or commercial sources are not available, largely due to the analyte instability limitations that the invention addresses. Compliance to newer guidelines and improved comparability of results for analytical methodologies are increasingly requiring the use of certified reference standards from independent sources when available and not those from laboratory-made materials prepared by the chemist performing the measurement.

Laboratories have utilized a range of specialized containers for chemicals associated with GC applications with cylindrical glass vials as the most common choice for test samples. Amongst these, a common choice is the "VOA" vial. It is a nominal 40 mL tall vial with a crimp or screw-top, ported (open topped) cap with a relatively soft elastomer septum typically a chlorobutyl rubber or silicone. Many commercial autosamplers are designed to hold this vial type, while the cap and the septum allows for needle piercing for sample collection using a syringe and delivery of that volume to the sample introduction apparatus of the GC instrument. In addition, traditional non-septum capped vials with various cap liners are also common in which the container is opened and a sample collected by a syringe or other means prior to delivery to the sample introduction apparatus of the GC instrument. Caps on containers are multi-part systems composed of a relatively rigid outer portion which is present primarily to apply pressure of the liner onto the lip of the container. The composition of this relatively rigid portion may be thermoplastic materials (e.g. polypropylene) or thermoset material (e.g. phenolic material) or even metallic material (e.g. aluminum). Sealing of the contents into the container is a relatively important component of any container system and currently available designs are not understood to satisfy the needs for storage of VOC's in water beyond a week (unpreserved) or two (preserved, pH<2) before measurable loss of analyte occurs by way of the cap liner and samples would be considered "expired" according to ASTM Method 8028. For example, polytetrafluoroethylene faced septa and cap liners are commercially available. However the layer of poly(tetrafluoroethylene) or PTFE is reportedly limited in its ability to form a layer impermeable to VOC's for a relatively extended storage period and thus does not address current need to improve the time period from sample or standard collection and closure to analytical analysis.

Accordingly, a need remains to provide a container cap liner for vials containing volatile and gas compounds so that storage stability is improved and better-quality analytical analysis is achieved. In particular, a need remains to provide such a cap liner for liquid samples that are stored in a vial that improves retention of gases and volatile organic compounds to improve the accuracy of groundwater testing. In addition, a need remains to provide a collection vial that will sufficiently seal the contents of collected samples so that gases and VOCs are preserved at acceptable levels for ensuing analytical evaluation and that will accommodate the production, distribution and use of reference materials for inter-laboratory "performance testing" (PT) for statistical cross comparability of measurements desired by private and public institutions.

Furthermore, with respect to environmental impact in groundwaters, methane is the gas of most interest. These liquids may or may not have a preservative added to the sample, e.g. pH adjusted to <2 using sulfuric acid is common. The addition of preservatives such as that mentioned emphasizes the requirement of a container system with low chemical reactivity to corrosives or other components found in groundwaters. Stability of analyte concentration encompasses many factors (e.g., loss due to time and conditions including shipping, bottle to bottle inhomogeneity from packaging processes, experimental (method) error); however for EPA GC applications +/−15% is typically the acceptance criteria for calibration stability and values for independent control samples. Hence, there is a need to achieve a loss component of methane within a storage vial to a level of less than 15%, preferably at less than 5.0% of actual methane loss, over a period that accommodates improved shelf life duration.

SUMMARY

An analytical storage device comprising a container for storing a sample for testing which contains gases or volatile organic compounds. The container has a top opening and a rim surrounding the top opening. A cap including a liner for the container top opening is provided wherein the cap is configured to engage with the container and compress the liner against the container rim surrounding the container top opening. The liner comprises a layer of polyvinylfluoride or polyvinylidene fluoride and a layer of compressible material.

An analytical storage device comprising a container for storing a sample for testing which contains gases or volatile organic compounds. The container includes a top opening and a rim surrounding the top opening. A cap including a liner for the container top opening is provided wherein the cap is configured to engage with the container and compress the liner against the container rim surrounding the top opening. Retention of the initial concentration level of gases or volatile compounds within the container system and within experimental error was less than 10.0% loss over a period of 90 days for methane, ethane and ethylene.

In addition, the present invention relates to an analytic storage device comprising a container for storing methane for testing. Retention of the initial concentration of methane was maintained at a level of less than 10.0% loss over a period of 170 days.

BRIEF DESCRIPTION OF THE FIGURES

FIG. 4 illustrates a preferred vial.

FIG. 5 illustrates a preferred cap with a liner.

DETAILED DESCRIPTION OF THE PREFERRED EMBODIMENTS

Figure 1:
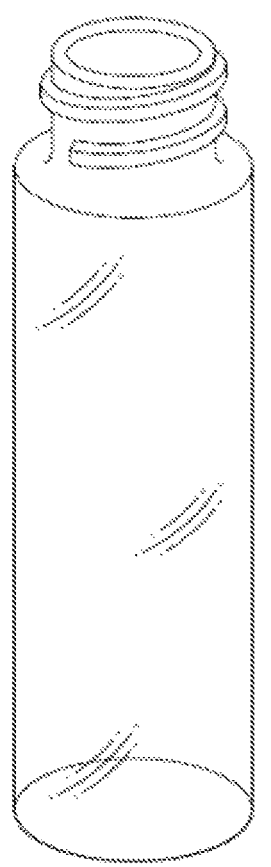
FIG. 1 is plot of gases methane, ethane, ethylene in water contained in a vial with a PTFE/silicone liner, illustrating percent recovery versus time.

The present invention relates to a cap liner for a vial (FIG. 4) that facilitates relatively long term stability and storage gases and various volatile compounds. The cap liner is such that it provides improved stability and storage of the gases and various volatile compounds over time for analytical analysis. The cap liner may preferably be positioned within a screw-cap or crimped-cap septa design that are typically employed in laboratory applications. See FIG. 5. As alluded to above, the cap itself may be formed from thermoplastic material (e.g. polypropylene), thermoset material (phenolic) or even metallic material (e.g., aluminum).

Gases and/or volatile organic compounds, that may be present in any liquid to be analyzed herein, include but are not limited to methane, ethane, ethane, and propane. Such VOCs when present in ground water can have health implications and relatively more accurate analytical testing is necessary. The analytical tools used for testing require frequent calibration and calibration verification with reference materials of the analyte(s) in a similar matrix, e.g. VOC's in water. To date, a limiting factor on the quality of the analytical data is the inability to store samples and calibrants with the necessary stability working time and shelf life.

Accordingly, reference to gases herein that may now be more efficiently stored for analytical testing purposes include compounds that have a MW of less than or equal to 70. As noted, such compounds therefore may include methane, ethane, ethylene, propane, or butane. In particular, methane is identified herein as a gas that is now more efficiently stored. Reference to VOCs is another way to characterize the compounds herein that are more efficiently stored for analytical testing purposes, and are understood to include compounds having a boiling point of less than or equal to 250° C. measured at standard atmospheric pressure. In addition, the storage of such gases or VOCs may be such that they are present in a liquid medium, such as water.

The cap liner and container system herein preferably demonstrates shelf lifetimes that support a change in the analytical methodology from requiring recent or freshly prepared standards to ones that can be managed as off the shelf standards as well as the procurement and use of independent reference standard materials. The cap liner and container system design preferably features a conventional glass body with open upper lip on which a liner is sealed using pressure from a screw cap or crimping device or any other mechanical type engagement. The cap liner herein is preferably constructed utilizing a viscoelastic backing material, a bonding adhesive, and a layer of poly(vinyl fluoride) (PVF) or poly(vinylidene fluoride) (PVDF) that forms the seal with the bottle lip.

Expanding upon the above, the container body is preferably a relatively rigid material bottle or vial type suitable for containing liquids or gas materials by being relatively non-permeable and chemically non-reactive. The cap is preferably a threaded, crimped or other mechanically applied cap composed of a relatively rigid material which may or may not be of different material composition than that of the container. The cap is selected such that it can apply a force to seal the cap to the container as found in conventional bottle containers.

As noted, the liner is preferably composed of PVF or PVDF. It is worth noting that such polymeric materials are particularly preferred as they offer the disclosed sealing performance herein and are also chemically non-reactive to acids/bases, such that they do not contaminate the downstream analytical testing procedures that are ultimately utilized. Such liner is then preferably adhered to a compressible backing material which preferably provide continuous compression force to the fluoropolymer against the rim of the container to form a liquid tight seal. With proper force or torque applied a relatively impermeable membrane seal, with respect to volatile and gas compounds can now formed with the container body.

Figure 2:
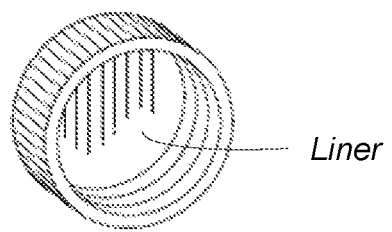
FIG. 2 is a plot of gases methane, ethane, ethylene in water contained in a vial with a PVDF/silicon liner, illustrating percent recovery versus days after packaging.
Figure 3:
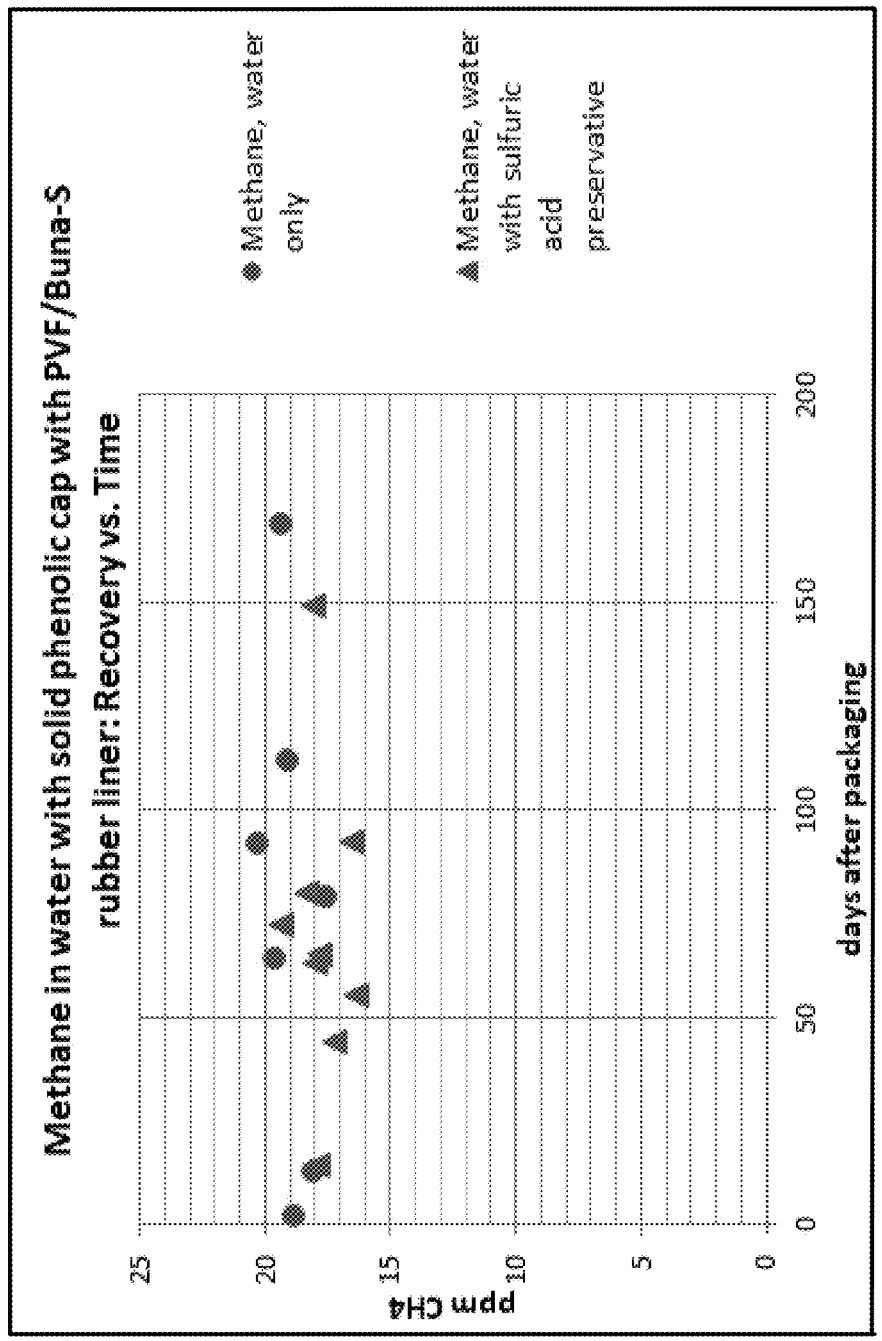
FIG. 3 is a plot of the gas methane contained in a vial with a PVF/Buna-S rubber liner illustrating ppm methane versus days after packaging.

Attention is directed to FIGS. 1-3 which identifies the sealing efficiency of the liner herein as compared to liners made of PTFE. More specifically, FIG. 1 is a plot of experimental data for current state of the art and common VOA vial showing significant loss of analyte in as few as ten days. Relative percent recovery of measured values are shown for methane, ethylene and ethane at prepared concentrations of 7 ppmw (nominal) in which the initial measurement is ascribed as 100%. Results extend to 85 days post production. This container is currently specified in analytical methodologies (e.g. ASTM D8028) and recommended refrigerated conditions were employed. 40 mL glass VOA vial features a polypropylene cap with liner composed of a PTFE faced, chlorobutyl rubber backing layer. Measurements employed a Shimadzu 2010 gas chromatographic analysis of the headspace above a sample. In headspace analysis, an appropriate volume of sample is transferred to an empty container of known volume and sealed. The container is agitated for a period of time to allow the analytes to partition into the headspace above the sample. A known volume of the gas in the headspace is injected into the gas chromatograph for separation of the individual components.

FIG. 2 is a plot of experimental data for the present invention container system featuring a 0.076 mm PVDF faced, 3.2 mm silicone backing layer onto a hollow capped, 40 mL glass VOA vial. Relative percent recovery of measured values are shown for methane, ethane, ethane at prepared concentrations of 7 ppmw (nominal) in which the initial measurement is ascribed as 100%. The individual percentage values shown in FIG. 2 vary slightly in both the positive and negative direction due to normal experimental factors common with time-separated measurements performed with strict attention to duplication of technique and carefully prepared yet independent calibrants. Results for recovery extend to about 90 days post production and suggest that experimental error and not loss was the dominant factor during that entire timeframe unlike FIG. 1 data where analyte loss clearly existed. Measurements employed a Shimadzu 2010 gas chromatographic analysis of the headspace above a sample. In headspace analysis, an appropriate volume of sample is transferred to an empty container of known volume and sealed. The container is agitated for a period of time to allow the analytes to partition into the headspace above the sample. A known volume of the gas in the headspace is injected into the gas chromatograph for separation of the individual components.

FIG. 3 is a plot of experimental data of concentration for an 18 ppmw (nominal) methane single-compound solution using the present invention container system. The container system features a 0.051 mm PVF faced, 1.5 mm styrene-butadiene (Buna-S) backing layer and 24 mL Wheaton brand glass vial with solid phenolic (conventional) cap. Consistent concentration measurements are indicated for greater than 149 days post-preparation for the two examples plotted. The first set of samples (round datapoints) were prepared as a gas mixture with neat deionized water and the second set of samples (triangle datapoints) were prepared identically; however with 0.16% sulfuric acid preservative added. Measurements employed a Shimadzu 2010 gas chromatographic analysis of the headspace above a sample. In headspace analysis, an appropriate volume of sample is transferred to an empty container of known volume and sealed. The container is agitated for a period of time to allow the analytes to partition into the headspace above the sample. A known volume of the gas in the headspace is injected into the gas chromatograph for separation of the individual components.

As can be seen from FIG. 2, over a storage period of about 90 days, the liner herein restricts the loss of gases or volatile compounds to a level of less than or equal to 10.0%. As may therefore be appreciated, laboratory prepared standards and groundwater samples collected in the field for the determination of the most volatile primary single and bi-carbon unit VOC gases can now be stored for a period of up to 3 months. In addition, as can also now be seen from FIG. 3, in the particular case of methane, such compounds can now be stored for a period of up to at least 170 days with a loss of less than or equal to 10.0%, more preferable, at a loss level of less than or equal to 5.0%.

It is worth noting that liner thickness herein is directly associated with gas permeability while indirectly associated with needle piercing properties. Preferably, as noted, the liner is one that includes a layer of PVF or PVDF and a compressible backing layer, where such backing layer applies a compression force to the liner material against the container rim. The PVF or PVDF is preferably present at a layer thickness in the range of 0.01 mm to 0.1 mm. The thickness of the backing layer is preferably in the range of 1.0 mm to 5.0 mm. The compressible backing layer is preferably a chlorobutyl rubber material or silicone elastomer at the durometer range of 30 A to 90 A. Other backing materials are contemplated to include ethylene-propylene rubber, ethylene-propylene-diene rubber, nitrile rubber, polychloroprene rubber (Neoprene™), styrene-butadiene rubber and fluoroelastomer (Viton™).

The compressible backing layer is preferably adhered to the PVF or PVDF by adhesive bonding. Such adhesive may preferably include the use of cyanoacrylates (e.g. 3M Scotchweld CA50), silicone base adhesives (e.g. 3M 5200), bonding tapes (e.g. 3M 9731) or other suitable adhesive materials (e.g. 3M Super 77 Adhesive), including their surface preparation processes that may include activators or primers (e.g. 3M AC79) or plasma treatments. The backing layer provides a compressive force on the liner to the container lip when the cap or crimp is suitably applied. Preferably, the adhesive and the backing layer are such that they allow for unhindered needle piercing with conventional syringe needles employed for GC instrumentation. Such syringe needles typically include 22 gauge (0.72 mm O.D) and can be found on GC autosamplers (Teledyne Tekmar, EST, OI Analytical).

What is claimed is:
1. An analytical storage device comprising:
a container for storing a sample for testing containing gases or volatile organic compounds, the container having a top opening and a rim surrounding the top opening;
a cap including a liner for said container top opening, wherein said cap is configured to engage with said container and compress said liner against said rim surrounding the top opening of said container;
said liner comprising a layer of polyvinylfluoride or polyvinylidene fluoride at a thickness of 0.01 mm to 0.1 mm and a layer of compressible material at a thickness of 1.0 mm to 5.0 mm selected from the group consisting of a chlorobutyl rubber, a silicone elastomer, ethylene-propylene rubber, nitrile rubber, polychloroprene rubber, styrene-butadiene rubber and a fluoroelastomer.

2. The analytical storage device of claim 1 wherein the gases comprise one or more of methane, ethane, ethylene, propane or butane.

3. The analytical storage device of claim 1 wherein the volatile organic compound comprises compounds having a boiling point of less than or equal to 250° C. measured at standard atmospheric pressure.

4. The analytical storage device of claim 1 wherein the compressible material is chlorobutyl rubber.

5. The analytical storage device of claim 1 wherein the compressible material is a silicone elastomer.

6. The analytical storage device of claim 1 wherein the compressible material is ethylene-propylene rubber.

7. The analytical storage device of claim 1 wherein the compressible material is nitrile rubber.

8. The analytical storage device of claim 1 wherein the compressible material is polychloroprene rubber.

9. The analytical storage device of claim 1 wherein the compressible material is styrene-butadiene rubber.

10. The analytical storage device of claim 1 wherein the compressible material is a fluoroelastomer.

11. An analytical storage device containing an initial level of gases or volatile compounds comprising:
    a container for storing a sample for testing containing gases or volatile organic compounds, the container having a top opening and a rim surrounding the top opening;
    a cap including a liner for said container top opening, wherein said liner comprises a layer of polyvinyl fluoride or polyvinylidene fluoride at a thickness of 0.01 mm to 0.1 mm and a layer of compressible material at a thickness of 1.0 mm to 5.0 mm wherein said cap is engaged with said container and compresses said liner against said rim surrounding the top opening of said container;
    wherein the initial level of gases or volatile compounds contained in the container is retained at a level of less than 10.0% loss over a period of 90 days and wherein the gases comprise one or more of methane, ethane, ethylene, propane or butane.

12. The analytical storage device of claim 11 wherein the volatile organic compounds comprises compounds having a boiling point of less than or equal to 250° C. measured at standard atmospheric pressure.

13. An analytical storage device containing an initial level of methane comprising:
    a container for storing a sample for testing containing methane, the container having a top opening and a rim surrounding the top opening;
    a cap including a liner for said container top opening wherein said liner comprises a layer of polyvinyl fluoride or polyvinylidene fluoride at a thickness of 0.01 mm to 0.1 mm and a layer of compressible material at a thickness of 1.0 mm to 5.0 mm, wherein said cap is engaged with said container and compresses said liner against said rim surrounding the top opening of said container;
    wherein the initial level of methane contained in the container is retained at a level of less than 10.0% loss over a period of 170 days.

14. The analytical storage device of claim 13 wherein the initial level of methane contained in the container is retained at a level of less than 5.0% loss over a period of 170 days.

* * * * *